(12) United States Patent
Sato et al.

(10) Patent No.: US 8,866,075 B2
(45) Date of Patent: Oct. 21, 2014

(54) APPARATUS PREPARING SAMPLES TO BE SUPPLIED TO AN ION MOBILITY SENSOR

(75) Inventors: Tomoyoshi Sato, Tsukuba (JP); Prakash Sreedhar Murthy, Tsukuba (JP)

(73) Assignee: Atonarp Inc., Tokyo (JP)

( * ) Notice: Subject to any disclaimer, the term of this patent is extended or adjusted under 35 U.S.C. 154(b) by 50 days.

(21) Appl. No.: 13/820,109

(22) PCT Filed: Aug. 31, 2011

(86) PCT No.: PCT/JP2011/004861
§ 371 (c)(1),
(2), (4) Date: Jul. 12, 2013

(87) PCT Pub. No.: WO2012/029303
PCT Pub. Date: Mar. 8, 2012

(65) Prior Publication Data
US 2013/0277547 A1  Oct. 24, 2013

(30) Foreign Application Priority Data

Aug. 31, 2010 (JP) ................. 2010-193382
Oct. 29, 2010 (JP) ................. 2010-243961

(51) Int. Cl.
*H01J 49/02* (2006.01)
*H01J 49/04* (2006.01)
*G01N 27/62* (2006.01)
*H01J 37/08* (2006.01)
*G01N 1/38* (2006.01)
*G01N 1/28* (2006.01)

(52) U.S. Cl.
CPC . *H01J 37/08* (2013.01); *G01N 1/38* (2013.01); *G01N 2001/2893* (2013.01); *G01N 27/624* (2013.01); *H01J 49/022* (2013.01); *H01J 49/04* (2013.01)

USPC .......................................... 250/288; 250/282

(58) Field of Classification Search
CPC . H01J 49/004; H01J 49/0027; H01J 49/0031; H01J 49/0095; H01J 49/02; H01J 49/022; H01J 49/04; H01J 49/0422; H01J 49/0427
USPC ........................................ 250/281, 282, 288
See application file for complete search history.

(56) References Cited

U.S. PATENT DOCUMENTS 6,835,313 B2  12/2004  Sando et al.
2005/0253061 A1 * 11/2005  Cameron et al. .............. 250/287
(Continued)

FOREIGN PATENT DOCUMENTS

JP  2002-243599 A  8/2002
JP  2002-361002 A  12/2002
(Continued)

OTHER PUBLICATIONS

International Search Report (PCT/ISA/210) issued on Dec. 6, 2011, by the Japanese Patent Office as the International Searching Authority for International Application No. PCT/JP2011/004861.

*Primary Examiner* — Nicole Ippolito
*Assistant Examiner* — David E Smith
(74) *Attorney, Agent, or Firm* — Buchanan Ingersoll & Rooney PC

(57) ABSTRACT

There is provided an analysis apparatus including a unit for preparing a sample gas to be supplied to an ion mobility sensor and a control unit equipped with a function of controlling the unit that prepares the gas. The unit for preparing the gas includes a concentration adjusting mechanism that changes the concentration of the target chemical included in the sample gas, and the control unit includes a driver that acquires a measurement result of the ion mobility sensor and a flow control unit that controls the concentration adjusting mechanism in a direction where is improvement in the measurement result.

18 Claims, 11 Drawing Sheets

(56) References Cited

U.S. PATENT DOCUMENTS

| | | |
|---|---|---|
| 2006/0104827 A1 | 5/2006 | Shaw et al. |
| 2006/0127237 A1 | 6/2006 | Shaw et al. |
| 2006/0192102 A1* | 8/2006 | Miller et al. .................. 250/286 |
| 2006/0192103 A1* | 8/2006 | Landgraf ....................... 250/287 |
| 2009/0032701 A1* | 2/2009 | Rodier ........................... 250/282 |
| 2011/0006196 A1 | 1/2011 | Boyle et al. |

FOREIGN PATENT DOCUMENTS

| | | |
|---|---|---|
| JP | 2005-291756 A | 10/2005 |
| JP | 2005-535893 A | 11/2005 |
| JP | 2005-535894 A | 11/2005 |
| JP | 2006-292508 A | 10/2006 |
| JP | 2008-508693 A | 3/2008 |
| WO | WO 2006/013396 A2 | 2/2006 |
| WO | WO 2009/018305 A1 | 2/2009 |

* cited by examiner

APPARATUS PREPARING SAMPLES TO BE SUPPLIED TO AN ION MOBILITY SENSOR

TECHNICAL FIELD

The present invention relates to an apparatus preparing samples to be supplied to an ion mobility sensor.

BACKGROUND ART

In recent years, apparatuses called FAIMS (Field Asymmetric Ion Mobility Spectrometers) have been subject to attention as a technology for detecting and analyzing chemical substances with high sensitivity. Such apparatuses use a minute filter to detect changes in mobility of ionized chemical substances caused by changes in a DC voltage and an AC voltage applied to a sensor and are capable of specifying chemical substances according to the differences in the detection results.

Japanese Patent Publication No. 2008-508693 (WO2006/013396) discloses an ion mobility spectrometer having an ion filter in the form of at least one ion channel with a plurality of electrodes. With this ion mobility spectrometer, it is possible for a filler to selectively admit ion species according to a time-varying potential that is applied to conductive layers. Such potential has a drive field component and a transverse field component, and in a preferred embodiment, the respective electrodes contribute to the generation of components of both the drive field and the transverse field. Such device may be used even without a drift gas flow.

DISCLOSURE OF THE INVENTION

Technologies that measure ion mobility, as examples FAIMS (Field Asymmetric waveform Ion Mobility Spectrometry) and DIMS (Differential Ion Mobility Spectrometry) are capable, even in a background that uses normal air, of isolating, detecting, and analyzing isomers of the same molecular weight, such as trace amounts of xylene. Accordingly, technologies that measure ion mobility in gas or air have an extremely high potential and have high expectations for use in a variety of applications. When applying measurement of ion mobility to analysis of trace amounts of chemical substances, it is known that variations in the environmental conditions of temperature, humidity, pressure, and the flow rate of the measured gas and variations and changes in the combination of chemical substances being measured have non-negligible effects on the reproducibility and precision of measurement results.

FAIMS technology ionizes the chemical substances to be measured and uses the property that ion mobility is unique to each chemical substance. During measurement, a sample (sample gas) is supplied, or a sample and a carrier gas (buffer gas) are supplied, to an ion mobility sensor with a function of forming an electric field, and a differential voltage (or "DV", "Dispersion Voltage", "Vd voltage", "AC voltage", "electric field voltage Vrf", hereinafter simply "Vf") and a compensation voltage (or "CV", "Vc voltage", "compensation voltage", "DC voltage", hereinafter simply "Vc") that control the electric field are changed to alternately and asymmetrically switch between a high electric field and a low electric field. By doing so, during flight, chemical substances aside from the target collide with the electrodes (plates) that generate the electric field and +ions or −ions are lost and not detected. On the other hand, if the conditions of the voltage Vf and the voltage Vc are appropriately controlled, it is possible to enable the ionized chemical substance that is the detection target to reach and collide with a detector.

By controlling the conditions of the electric field using software, AD converting the minute currents that are detected at such time, and inputting such as voltage values, it is possible to detect and analyze target chemical substances.

One aspect of the present invention is an apparatus including a unit of preparing a sample to be supplied to an ion mobility sensor and a control unit including a function of controlling the unit of preparing (preparation unit). The unit of preparing includes a concentration adjusting mechanism changing a concentration of a first composition (component, constituent) included in the sample, and the control unit includes a function (functional unit) of acquiring a measurement result of the ion mobility sensor and a function (functional unit) of controlling the concentration adjusting mechanism in a direction in which the measurement result improves. This apparatus (device) may be an analysis apparatus including the ion mobility sensor and a processing unit that obtains an analysis result based on an output of the ion mobility sensor and control information sending to the concentration adjusting mechanism, or may be provided as a preprocessing apparatus of a sample (sample gas) to be supplied to an ion mobility sensor.

In an ion mobility sensor, if the concentration of the ionized chemical substance to be measured exceeds a given level, a measurable range of current values is exceeded and the measurement precision falls. On the other hand, if the concentration of the ionized chemical substance to be measured is too low, separation from the background is difficult. In this apparatus, by automatically adjusting the concentration of a first constituent that is or should be the object to be measured included in the sample, it is possible to keep the concentration of the first constituent within the measurement range of the ion mobility sensor. In addition, by controlling the concentration of the first constituent in the sample, conditions that facilitate separation from the background and facilitate separation from other compositions (constituents) in the sample are found, which makes it possible to improve the measurement precision and/or reproducibility.

The control unit should preferably include a function (functional unit) of accessing a database of a plurality of chemical substances that are to be measured by the ion mobility sensor and includes concentration data on concentrations of each of the plurality of chemical substances that facilitate detection by the ion mobility sensor and for controlling the concentration adjusting mechanism to produce a concentration suited to a chemical substance included in the measurement result. The control unit may include a function (functional unit) of controlling the concentration adjusting mechanism so as to change a concentration of the first constituent in stages (step-by-step, gradually). It is possible to automatically find a concentration at which the measurement result improves. The control unit may include a function (function unit) of outputting control information outputted or sent to the concentration adjusting mechanism to other unit or other purpose.

The concentration adjusting mechanism should preferably include an adsorption material that adsorbs the first composition and a mechanism that heats the adsorption material to emit (release) the first composition adsorbed by the adsorption material to the carrier gas, and the control unit should preferably include a function (functional unit) of controlling the temperature of the adsorption material. By controlling the temperature of the adsorption material, it is possible to increase the concentration of the first constituent in the sample. The concentration adjusting mechanism should preferably further include a first path where a first gas that includes the first constituent passes the adsorption material and a second path where a constituent adsorbed by the adsorption material is released to the carrier gas, and the control unit should preferably include a function (functional unit) of controlling a period for which the adsorption material is exposed to the first gas. The concentration adjusting mechanism should preferably include a plurality of the first paths and the second paths, and the control unit should preferably include a function (functional unit) of controlling the plurality of the first paths and the second paths according to time division. It becomes possible to carry out measurement continuously while concentrating the first composition in the sample.

The concentration adjusting mechanism may include a third path feeding back the first gas to the first path. The adsorption material may be porous glass. By using porous glass with a high probability of including holes of an appropriate diameter for the first composition, it is possible to selectively concentrate the first composition.

It is also effective for the concentration adjusting mechanism to include a mechanism that incorporates the first constituent into the sample by heating a liquid including the first constituent and for the control unit to include a function (functional unit) of controlling a heating temperature of the liquid including the first composition. It is also effective for the concentration adjusting mechanism to include a mechanism that incorporates the first constituent into the sample by ejecting a liquid including the first constituent according to an ink-jet method and for the control unit to include a function (functional unit) of controlling the ejected amount of liquid including the first constituent. It is possible to control the concentration of the first constituent (composition) in the sample.

It is also effective for the concentration adjusting mechanism to include a mechanism that removes a second constituent (composition) from the first gas including the first constituent (composition) to lower the concentration of the second constituent in the first gas. The second constituent is moisture, for example. Also, in a case where air is used as the carrier gas, by controlling the concentration of oxygen, nitrogen or carbon dioxide, it is possible to indirectly increase the concentration of the first constituent and to suppress changes in composition due to the first constituent reacting with oxygen, nitrogen, or the like during measurement.

It is also effective for the concentration adjusting mechanism to include a flow amount control mechanism for injecting a first gas including the first constituent into the carrier gas and for the control unit to include a function (function unit) for changing a mixing ratio of the first gas and the carrier gas using the flow amount control mechanism. A typical carrier gas is air or a gas with a known composition.

It is also effective to further include a mechanism causing a constituent to be analyzed to react with another composition or constituent to convert to or generate a constituent including the first constituent. If the composition to be analyzed is corrosive, poisonous, is highly reactive with the carrier gas, makes it difficult to improve the sensitivity of the ion mobility sensor, or the like, it is desirable to carry out measurement having converted the constituent to be analyzed via a chemical reaction or the like.

If a gas collecting apparatus that collects gas to be analyzed which includes the first constituent and supplies the gas to the concentration adjusting mechanism includes a unit that controls an air amount forming an air curtain and a unit that collects the gas to be analyzed from a region surrounded by the air curtain, the control unit should preferably include a function (functional unit) of controlling, in cooperation with the concentration adjusting mechanism, the air amount forming the air curtain.

It is also effective for the apparatus to further include a calibration unit that incorporates a pilot composition including a known chemical substance into the sample. One embodiment of the calibration unit supplies the pilot composition in place of the first composition to the concentration adjusting mechanism.

Another aspect of the present invention is a control method for an apparatus including a unit of preparing a sample to be supplied to an ion mobility sensor and a control unit controlling the unit of preparing. The unit of preparing includes a concentration adjusting mechanism changing a concentration of a first constituent (composition) included in the sample. The control method includes the following steps:

the control unit receiving a measurement result from the ion mobility sensor; and the control unit controlling the concentration adjusting mechanism in a direction in which the measurement result improves.

One method of controlling the concentration adjusting mechanism includes the control unit accessing a database of a plurality of chemical substances that are to be measured by the ion mobility sensor and includes concentration data on concentrations of each of the plurality of chemical substances that facilitate detection by the ion mobility sensor and controlling the concentration adjusting mechanism to produce a concentration suited to a chemical substance included in the measurement result. The method may include the control unit controlling the concentration adjusting mechanism so as to change a concentration of the first constituent in stages.

This control method can be recorded on a suitable recording medium or provided via a network as software (a program or a program product) so as to enable execution by a computer with suitable hardware resources.

DETAIL DESCRIPTION

Figure 1:
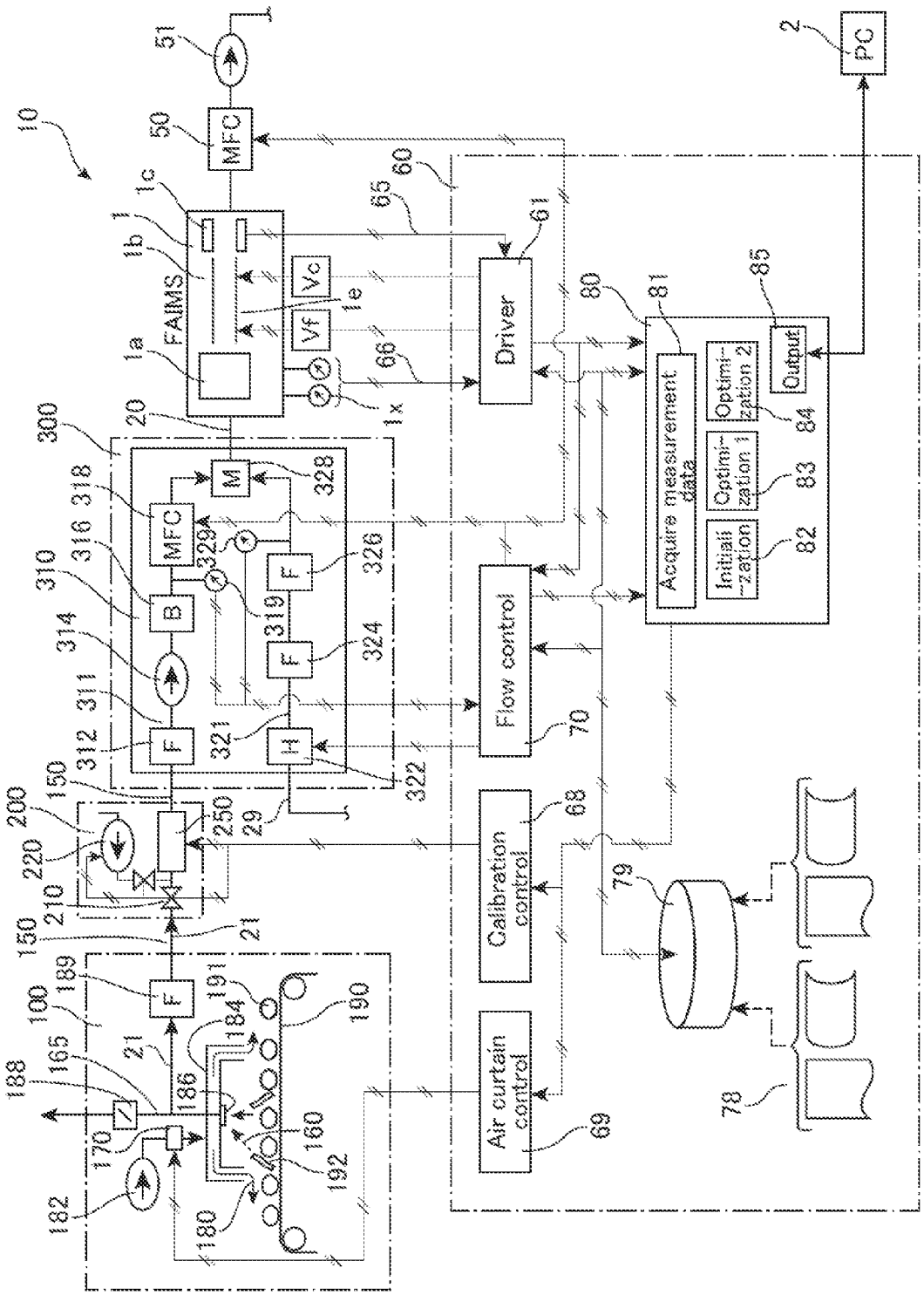
FIG. 1 is a block diagram showing an overview of an analysis apparatus.

FIG. 1 shows an overview of a measurement/analysis system equipped with a FAIMS (ion mobility sensor). This measurement/analysis system (or measurement analysis apparatus hereinafter simply "analysis system" or "analysis apparatus") 10 includes, from an upstream side thereof, a sampling unit 100 that collects a gas ("target gas" or "first gas") 21 to be analyzed, a calibration unit 200 that injects a pilot chemical into a sampling line, a preparation unit 300 that prepares sample gas 20 to be supplied to a FAIMS (sensor) 1, the FAIMS 1, a flow controller 50 that controls the amount of gas flowing to the FAIMS 1, a suction pump 51 that draws and discharges the sample gas 20, and a control unit 60 that controls the analysis apparatus 10.

The FAIMS 1 includes an ionizing unit 1a that ionizes a target chemical substance (or "measured object" or "object"), a drift chamber 1b that transfers the ionized measured object while applying the effects of an electric field to the ionized measured object, and a detector 1c that detects the ionized measured object (electric charge to be measured) that has passed through the drift chamber 1b. In the drift chamber 1b, the electric field generated by the electrodes 1e and controlled by software changes between positive and negative with a specified cycle, and due to the filtering effect of such electric field, chemical substances that are the detection targets are filtered, collide with the detector 1c, and a measured as electric currents in a short period, for example, at msec (millisecond) level.

One example of a FAIMS 1 is a sensor made by Owlstone, with Ni63 (a 555 MBq β source, 0.1 μSv/hr) being used in the ionizing unit 1a. The chemical substances that can be ionized by the ionizing unit 1a have an ionization binding energy of 67 KeV or below, which means that it is possible to detect and analyze a wide range of chemical substances. Devices that use UV, devices that use corona discharge, and the like are being investigated as the ionizing unit 1a.

The control unit 60 includes a driver 61 that controls the sensor 1. Measurement conditions are sent from the driver 61 to the sensor 1. The measurement conditions include the field voltage Vf (hereinafter simply "voltage Vf") and the compensation voltage Vc. The driver 61 acquires the measured data (IMS data) 65 from the sensor 1. One example of the IMS data 65 is a spectrum expressed by a current (the ion current detected by a detector 1c) I that changes corresponding to variations in the compensation voltage Vc at a specified voltage Vf. The IMS data 65 may be data produced by sampling (extracting) feature points of the spectrum described above or may include spectra of a plurality of voltages Vf. The driver 61 also acquires information 66 on the measurement environment of the sensor 1. The measurement information 66 includes temperature, humidity, pressure, flow rate, and the like, with a sensor 1x for detecting such information being provided in the sensor 1.

The preparation unit 300 that prepares the sample gas 20 includes a concentration adjusting mechanism 310 that adjusts the concentration of a target composition (or "first constituent" or "first composition") included in the sample gas 20. The concentration adjusting mechanism 310 includes hardware for controlling the concentration. More specifically, the concentration adjusting mechanism 310 includes a path (sample gas line) 311 that handles a target gas (or "first gas") 21 including the target composition and a path (or "carrier gas line") 321 that handles a carrier gas 29 to be mixed with the target gas 21. A typical example of the carrier gas 29 is air, and unless stated otherwise, the carrier gas 29 in the following description is air. The carrier gas 29 may be nitrogen or an inert gas such as argon. The carrier gas 29 may be a dopant that includes a constituent that is effective for separating peaks of the target composition that is to be analyzed.

The sample gas line 311 includes, from the inlet side, a particle filter 312, a pump 314, a buffer 316, and a mass flow controller 318. The carrier gas line 321 includes a dehumidifier unit 322, a hydrocarbon scrubber 324, and a particle filter 326. The target gas 21 that has passed the sample gas line 311 and the carrier gas 29 that has passed the carrier gas line 321 are mixed by a mixer 328 to generate the sample gas 20. The hydrocarbon scrubber 324 adsorbs hydrocarbon compounds in the carrier gas 29. A typical example of the dehumidifier unit 322 is a molecular sieve.

The mass flow controller (MFC) 318 is an appliance that measures the mass flow rate of a fluid and carries out flow control, with a digital MFC being used in the concentration adjusting mechanism 310. Volume flow rate and mass flow rate are mainly used to measure the flow rate of the fluid. If there is a change in volume due to changes in environmental temperature and usage pressure for the fluid to be measured, the volume flow rate is corrected in keeping with such degree of change in order to accurately measure the flow rate. With the mass flow rate, by measuring the mass (weight) of a fluid, there is no need for correction in response to changes in usage conditions. The MFC 318 is a known device as a flow rate controller for a process, such as a semiconductor process, that requires highly precise measurement and control of flow rate.

The control unit 60 includes a flow control unit 70 that digitally controls the MFC 318. The flow control unit 70 further controls an MFC 50 that manages a flow on the discharge side of the sensor 1. Normally, the MFC 50 on the discharge side maintains a constant flow rate for the sensor 1 and the flow rate of the target gas 21 introduced into the carrier gas 29 is controlled by the MFC 318 for the target gas 21. Accordingly, it is possible to control the mixing ratio of the target gas 21 and the carrier gas 29 included in the sample gas 20 using the flow control unit 70.

The flow control unit 70 includes a function of monitoring the gas flow rates on the respective lines using gas flow rate sensors 319 and 329 provided on the sample gas line 311 and the carrier gas line 321 respectively. If the dehumidifier unit 322 includes a unit capable of adjusting humidity, for example a humidifier unit, the flow control unit 70 may also include a function of controlling the humidity of the sample gas 20 that passes through the sensor 1 by controlling the humidity of the carrier gas.

The concentration adjusting mechanism 310 includes a positive pressure pump 314 and controls the passing conditions of the sensor 1 in combination with a negative pressure pump 51 on the discharge side. The positive pressure pump 314 and the negative pressure pump 51 may be composed of two or more pumps connected in parallel. A buffer may also be provided on the discharge side of the sensor in addition to the buffer (sampling buffer) 316 on the input side of the sensor 1. By providing the buffer 316 and the plurality of pumps 314 and 51, it is possible to suppress fluctuations in the flow rate that passes the sensor 1 and to improve the measurement precision. Since present technology needs a flow rate of around 35 cc to 50 cc/sec for stable measurement, by providing a buffer region with around two to three times such amount, it is possible to alleviate causes of instability.

One example of small-scale pumps 314 is a TEFLON (registered trademark)-coated dry-type small pump, such as a plunger pump, a piston pump, a rotary pump, a roots pump, or a claw pump. The pump 314 on the upstream side of the sensor 1 functions as a pump (positive pressure pump) that pushes the gas toward the sensor 1 and the pump 51 on the downstream side functions as a pump (negative pressure pump) that draws gas from the sensor 1. For this reason, even if a degree of variation in flow rate, pulsation, and the like occur for the pumps 314 and 51, it is possible to suppress the variations and pulsation of the flow rate of the sample gas 20 flowing past the sensor 1. By constructing the pumps 314 and 51 from a plurality of pumps, it is also possible to control the flow rate of the sample gas 20 supplied to the sensor 1 and to control the pressure via on/off control of the pumps.

The flow control unit 70 is an inflow rate control circuit (automatic flow rate optimization apparatus) and controls the flow rate of the sample gas 20 flowing into the ion mobility sensor 1. The flow control unit 70 acquires signals from the gas flow rate sensors 319 and 329. In addition, the flow control unit 70 acquires, via the sensor driver 61, a signal from an internal flow rate sensor of the ion mobility sensor 1.

The flow control unit 70 refers to an optimization table 78 for automatic control included in a FAIMS database 79 and sets, in the MFC 318, an optimal flow rate for measuring a target composition or a target constituent included in the target gas 21 at the sensor 1. The database 79 may be included in the control unit 60 or may be included in a server or the like with which the control unit 60 is capable of communicating via a computer network or the like. The database 79 includes chemical substance group information, ion mobility, heat map information, statistical data, and prediction/simulation models. A flow rate control optimization table is included in the optimization table 78 for automatic control provided in the database 79, and by converting the target composition to a chemical substance group, inflow speed (flow rate) control, the ion mobility, and a measurement data (current value) correlation table are given.

Accordingly, the flow control unit 70 includes a function of increasing the measurement precision by fixing the flow speed (flow rate) of the sample gas 20 that passes the sensor 1. In addition, although there are cases where a range of the current value is exceeded at the sensor 1 due to the concentration of the chemical substances being measured, the flow control unit 70 includes a function that controls the concentration adjusting mechanism 310 so as to carry out control of the flow rate of the carrier gas 29 and control of the flow rate of the target gas 21 via software so that the concentration of the chemical substances to be measured included in the target gas 21 is within a range of concentration where precise detection by the sensor 1 is possible so as to improve the measurement results of the sensor 1. In this example, although the sample gas flow is controlled by the MFC 50, the target gas flow is controlled by the MFC 318, and the carrier gas flow is automatically controlled so as to be decided by such control, it is also possible to directly control the carrier gas flow using an MFC. Accordingly, tasks such as manually measuring and diluting samples are not required.

The control unit 60 includes a concentration control unit 80 that automatically adjusts concentration using the concentration adjusting mechanism 310. The concentration control unit 80 includes a unit (function) 81 that acquires a measurement result of the sensor 1 via the driver 61, a unit (function) 82 that makes initial settings of the concentration adjusting mechanism 310, a unit (function) 83 that carries out a first optimization, and a unit (function) 84 that carries out a second optimization. In addition, the concentration control unit 80 includes a unit (function) 85 that outputs control information outputted or sent to or being sending to the concentration adjusting mechanism 310, measurement results, and an optimization state to a host terminal 2 such as a personal computer.

Figure 2:
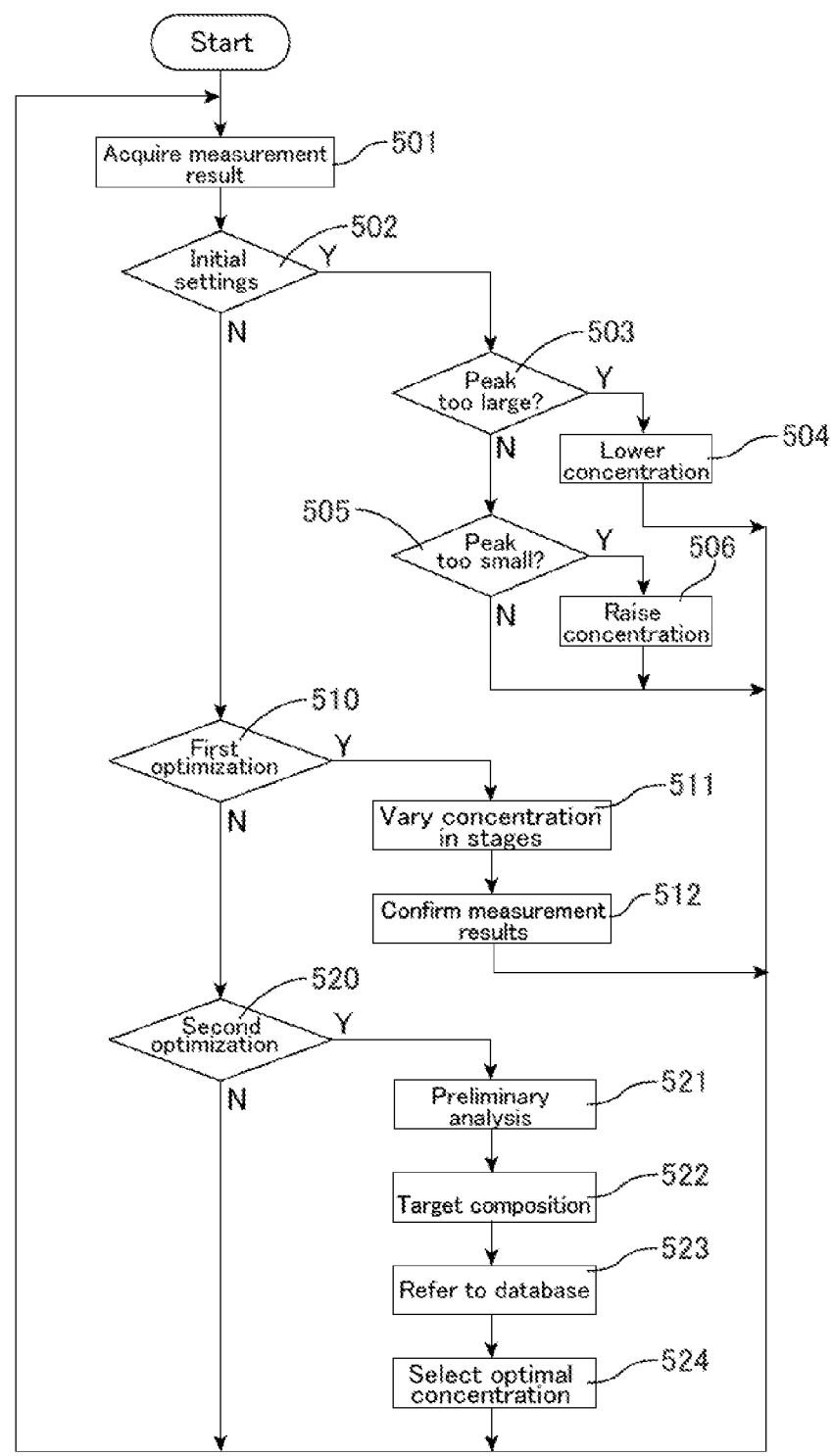
FIG. 2 is a flowchart showing one example of control of the analysis apparatus.

FIG. 2 shows a procedure for automatically adjusting the concentration of the sample gas 20 using the concentration control unit 80 by way of a flowchart. In step 501, the IMS data 65 of the sensor 1 is acquired by the unit 81 that acquires a measurement result. In an initial setting stage in step 502, the initial setting unit 82 roughly controls the target gas concentration. First, if, in step 503, the peaks included in the IMS data 65 are too large and exceed the measurement range, in step 504, the MFC 318 of the concentration adjusting mechanism 310 is controlled so as to reduce the concentration of the target gas 21 in the sample gas 20. On the other hand, if, in step 505, the peaks included in the IMS data 65 are too small and cannot be clearly established, in step 506, the MFC 318 of the concentration adjusting mechanism 310 is controlled so as to increase the concentration of the target gas 21 in the sample gas 20.

Once the initial settings have been completed and a concentration for which IMS data 65 with peaks included within a specified range is obtained has been established, the first optimization is carried out in step 510. First, in step 511, the first optimization unit 83 controls the MFC 318 of the concentration adjusting mechanism 310 so as to change the concentration of the target gas 21 in the sample gas 20 in stages. The range of concentration of the target composition suited to measurement in the ion mobility sensor 1 is of the order of ppb or ppt. Accordingly, although the dilution ratio of the target gas 21 will change according to the concentration of the target composition included in the target gas 21, control is carried out to change the concentration in at least ten stages within a range where measurement is possible. In addition, in step 512, the IMS data 65 at different concentrations is evaluated and a concentration within the sample gas 20 suited to the measurement of the target gas 21 is decided in even more detail.

Next, the second optimization is carried out in step 520. In step 521, the second optimization unit 84 carries out preliminary analysis of the obtained IMS data 65 and in step 522, selects a candidate for the composition (constituent, chemical substance) included in the target gas 21. The selected candidate is the final target composition for which adjustment of the concentration is carried out by the concentration adjusting mechanism 310. Once the target composition or constituent (chemical substance) has been selected, in step 523 the database 79 of a plurality of chemical substances to be measured by the ion mobility sensor 1 is referenced. As described earlier, an optimization table 78 for automatic control in which concentration data for easily detecting each of a plurality of chemical substances in an ion mobility sensor 1 is provided in the database 79. Accordingly, in step 524, a concentration that is suited to the chemical substance (target composition) included in the measurement result is acquired and the concentration adjusting mechanism 310 is controlled.

In this way, in the system according to the present embodiment, the concentration of the target gas 21 in the sample gas 20 is automatically adjusted to make it possible for the ion mobility sensor 1 to precisely detect the target composition included in the target gas 21. The automatic adjustment of concentration is not limited to the initial stage and adjustment of concentration may be carried out so as to automatically follow variations in the concentration of the target gas 21. Variations in the concentration of the target gas 21 can be discovered by analyzing the measurement results of the sensor 1. Accordingly, in the analysis apparatus (or the analysis system) 10, it is possible to analyze the target gas 21 while automatically searching for a sweet spot for the concentration where favorable analysis results are always obtained.

Precise management of the concentration and flow rate of the sample gas 20 that passes the ion mobility sensor 1 is important in order to improve the measurement precision of the sensor 1. To increase the measurement precision of the sensor 1, it is also important to carry out calibration correctly. To do so, a calibration unit that can be compactly installed, can suppress routine maintenance, and is capable of carrying out calibration automatically is desirable. For this reason, the automatic calibration unit 200 is provided in the analysis apparatus 10.

In the analysis apparatus 10, the automatic calibration unit 200 is built into a sampling line 150 that supplies the target gas 21 upstream of the concentration adjusting mechanism 310. Although this arrangement is favorable in that calibration of the concentration adjusting mechanism 310 can also be carried out using the calibration unit 200, the calibration unit 200 may be disposed upstream of the ion mobility sensor 1, may be disposed in series with the sampling line 150, or may be disposed in parallel with the sampling line 150.

That is, although the calibration unit 200 has a pilot composition (or "pilot chemicals" or "pilot constituents") including known chemical substances introduced into the sample gas 20 via the sampling line 150 that supplies the target gas 21 to the sensor 1, it is also possible to dispose the calibration unit 200 immediately before the sensor 1 so as to introduce the pilot chemicals into the sample gas 20.

The calibration unit 200 includes a valve system 210 that introduces the pilot chemicals into the sampling line 150 in place of the target gas 21, a calibration gas supply pump 220, and a unit 250 that introduces a pilot sample including the pilot chemicals. The control unit 60 also includes a unit that controls the calibration unit 200. The calibration unit 200 supplies the pilot chemicals in place of the target gas 21 that includes the target composition to the concentration adjusting mechanism 310.

Figure 3:
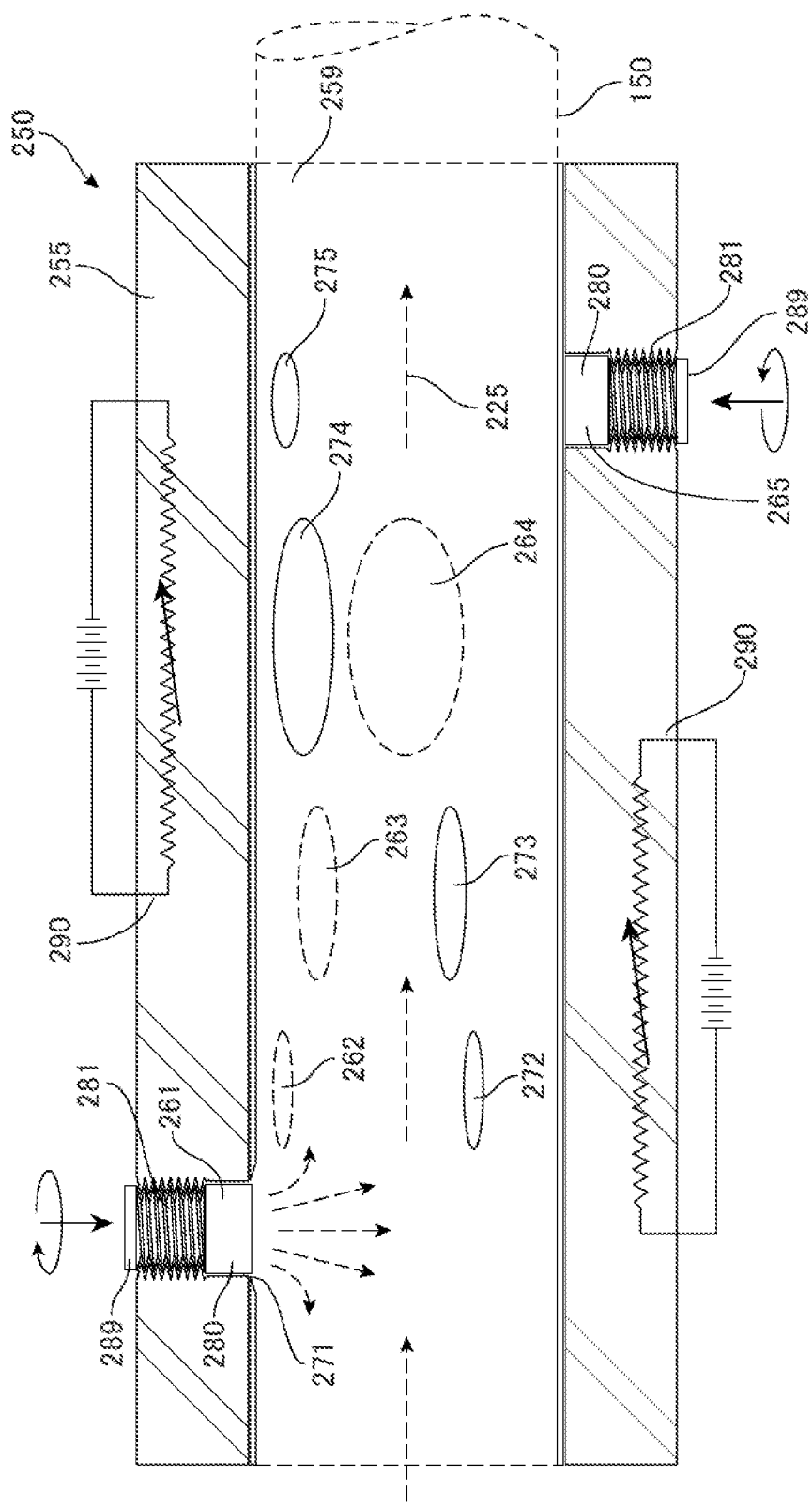
FIG. 3 is a cross-sectional view showing the skeleton framework of a sample introducing unit.
Figure 4:
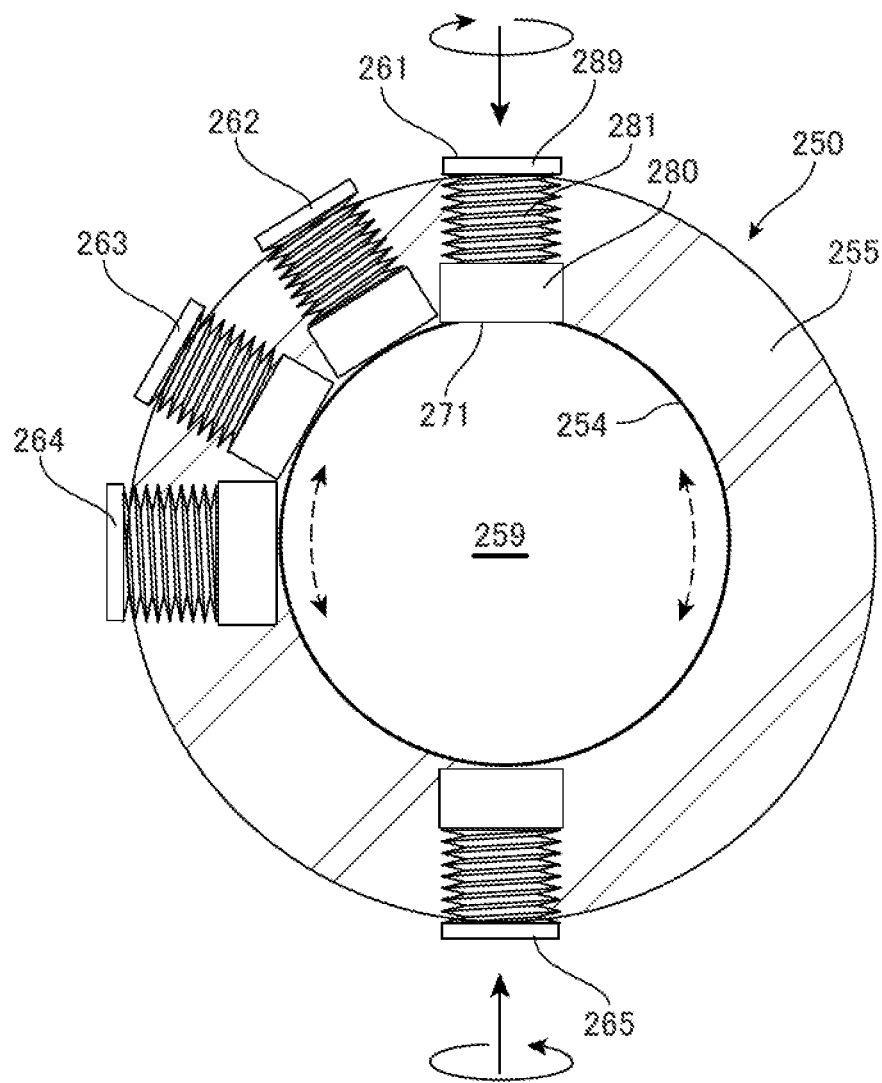
FIG. 4 is a cross-sectional view showing the skeleton framework of a sample introducing unit from another direction.

FIG. 3 shows the overall construction of the pilot sample introducing unit 250 by way of a cross-sectional view. FIG. 4 shows the pilot sample introducing unit 250 from the direction in which gas (calibration gas) flows.

The pilot sample introducing unit 250 has a cylindrical housing 255 that also serves as a pipe to which tubes (nanotubes) are installed, each tube filled (loaded) and sealed with a calibration pilot substance (or "pilot chemical") in advance and has a certain cross-sectional area and a certain depth to the housing 255. The housing 255 is then rotated in the manner of Russian roulette with a loaded gun and, according to software control, one of the tube-like pilot samples 261 to 265 appears in a space 259 inside the housing 255 and is selected as a pilot chemical used for calibration.

The concentration, molecular weight, and molecular structure are known in advance for the pilot chemicals sealed in the tubes of the pilot samples 261 to 265, and measurement results for such pilot chemicals are obtained in advance by the sensor 1 with various environmental conditions (including temperature, humidity, pressure, and flow rate). Accordingly, by comparing the actual measurement results for the sensor 1 (measured values) and values obtained in advance (theoretical values, standard values), it is possible to calibrate the measured values.

Although there are cases where depending on the composition used as the target, the chemical properties of the target gas 21, and the background (environment), calibration using one pilot sample is insufficient, with this unit 250, it is possible to select a plurality of pilot samples. Also, although there are also problems such as deterioration over time and complicated handling if the pilot samples are liquids, by using a type where the pilot samples 261 to 265 are sealed in respective tubes, it is possible to keep the pilot chemicals in a favorable state. In addition, by loading the respective tubes of the pilot samples 261 to 265 so as to be sealed in the housing 255, it is possible to minimize the contact area with the outside and to prevent problems such as oxidization, which means that it is possible to use a construction where a new sample surface appears when the pilot samples are actually used. Accordingly, in spite of being compact and having a simple construction, the unit 250 is capable of keeping pilot chemicals that are in a liquid or gaseous state in a condition with little deterioration over a long period just like solids, and is also capable of introducing fresh pilot chemicals into a line.

In more detail, the pilot sample introducing unit 250 includes a cylindrical inner housing (or simply "inner") 254 and an outer housing (or simply "outer") 255 that is concentrically disposed outside the inner 254 and rotates relative to the inner 254. Calibration gas 225 is supplied to the space 259 inside the inner housing 254 by the calibration gas supplying pump 220. The calibration gas 225 is typically air and is the carrier gas that supplies the pilot chemical to the sensor 1 via the sampling line 150.

On the outer housing 255, the pilot samples 261 to 265 that respectively include the tubes that contain the pilot chemicals used for calibration are disposed so to not overlap in the direction in which the calibration gas 225 flows. The tubes 261 to 265 are concentrically installed in the outer housing 255 on the outside of the inner 254. The inner 254 is provided with openings, for example the openings 271 to 275, at positions that coincide with the pilot samples 261 to 265. When the inner 254 and the outer housing 255 rotate relative to each other, one of the pilot samples 261 to 265 appears in the inner space 259 from one of the openings 271 to 275 and a pilot chemical is emitted to the calibration gas 225 from the tube of the exposed pilot sample. Accordingly, one of the pilot chemicals included in the pilot samples 261 to 265 is included in the sample gas 20 and is supplied to the ion mobility sensor 1.

The areas of the openings 271 to 275 corresponding to the pilot samples 261 to 265 respectively are changed, for example, if the area of the opening 271 of the pilot sample 261 is set as a standard (1.0), the area ratio of the opening 272 of the pilot sample 262 is 2.0, the area ratio of the opening 273 of the pilot sample 263 is 5.0, and the area ratio of the opening 274 of the pilot sample 264 is 10.0.

In the pilot sample introducing unit 250, the inner 254 and the outer 255 rotate relative to one another and when doing so, the inner 254 contacts the surface of each tube 280 of the pilot samples 261 to 265, resulting in the surfaces of the respective tubes 280 wearing away. The tubes 280 of each of the pilot samples 261 to 265 have pressure applied thereto in a direction from the outer housing 255 toward the inner 254 by a spring or a screw 281. By relatively rotating the inner 254, the surfaces of the tubes 280 are reliably worn away so that a surface of a tube that is always new will be exposed to the calibration gas 225.

One example of a tube 280 is porous glass including a large number of minute holes (holes with a diameter of an order of μm or nm), so that by grinding the surface of the glass, pilot chemicals that are always fresh can be emitted. The respective tubes 280 of the pilot samples 261 to 265 can be easily replaced by removing a cap 289 from outside the outer housing 255.

Four out of the pilot samples 261 to 265, for example the samples 261 to 264 include pilot chemicals such as respectively different indirectly detected reactive chemical substances and/or catalysts, oxygen, and the like. Accordingly, by rotating the inner 254 and/or the outer housing 255, depending on the rotational speed, different samples are exposed with different areas to the calibration gas 225. This means that it is possible to calibrate the ion mobility sensor 1 according to the type and concentration of gases ("samples" or "pilot chemicals").

The outer housing 255 may be equipped with a heater 290 for producing a temperature that facilitates the emission of samples. The pilot sample 265 is a pilot sample that emits a chemical substance TC (Terminal Chemical) indicating the end of calibration. Once the chemical substance TC has been emitted from the pilot sample 265 to the calibration gas 225 and has been detected by the ion mobility sensor 1, it is automatically determined that calibration has ended. Due to the pilot sample introducing unit 250 emitting the chemical substance TC, the calibration unit 200 informs the ion mobility sensor 1 and its analysis unit (control unit) 60 that the calibration process has ended.

In this way, it is possible to release a specified pilot chemical in place of the control signal to the sampling line 150 to control the analysis apparatus 10. For example, in a case where indirect detection is carried out, the chemical substance TC can be used as a signal to show that the chemical substances subject to a reaction have been entirely used. The chemical substance TC can also be used as a signal indicating an end of cleanup for the sampling line 150.

Returning to FIG. 1, the analysis system 10 collects the gas ("target gas" or "first gas") to be analyzed using the sampling unit 100. As one example, the sampling unit 100 is capable of collecting the target gas 21 from a conveyor 190 that conveys products of one or a plurality of types and identifying an article 191 being conveyed on the conveyor 190 and/or identifying foreign matter 192 that has the possibility of being included in the article 191. The sampling unit 100 forms an air curtain 180 to suppress the effects of the outside world on the target gas 21 and collects the target gas 21 from a region surrounded by the air curtain 180.

To do so, the sampling unit 100 includes a pump 182 for supplying air for the air curtain, a hood 184 for forming the air curtain 180, and a sampling nozzle 186 for collecting gas from inside the hood 184. In this example, a part of the air from the air curtain 180 is discharged via the nozzle 186 and some of such discharge 165 is drawn using the positive pressure pump 314 and collected as the target gas 21. It is also possible to provide a pump for collecting the target gas 21 in the sampling unit 100. It is possible to control the discharge amount using a damper 188 and the collected target gas 21 is supplied via an appropriate filter 189 to the sampling line 150.

There is the possibility that the target chemical (or first composition) 160 included in the target gas 21 collected by the sampling unit 100 will be affected by the amount of air forming the air curtain 180. As one example, if the amount of air in the air curtain 180 is too great, there is the possibility of the concentration of the target chemical 160 included in the target gas 21 falling, while if the amount of air in the air curtain 180 is too little, there is the possibility of an increase in noise (i.e., other chemicals) being included in the target gas 21. For this reason, the sampling unit 100 includes a flow control mechanism 170 that controls the amount of air in the air curtain 180, and the control unit 60 includes an air curtain control unit 69 that controls the amount of air using the flow control mechanism 170. One example of the flow control mechanism 170 is a damper, and the amount of air may be controlled by controlling the rotational speed of the pump 182.

The air curtain control unit 69 carries out coordinated control (collaboration control) of the amount of air in the air curtain 180 and the concentration adjusting mechanism 310. As one example, the air curtain control unit 69 increases the amount of air on determining that there is too much noise in the IMS data 65 and on determining that the concentration of the target chemical 160 included in the target gas 21 has fallen as a result, carries out control so that the flow control unit 70 uses the concentration adjusting mechanism 310 to raise the concentration of the target chemical 160 included in the sample gas 20. On the other hand, if a peak of the target chemical is not observed in the IMS data 65, the air curtain control unit 69 reduces the amount of air within a tolerated range to maintain an adjustment region (or "turndown ratio") for the concentration adjusting mechanism 310

Figure 5:
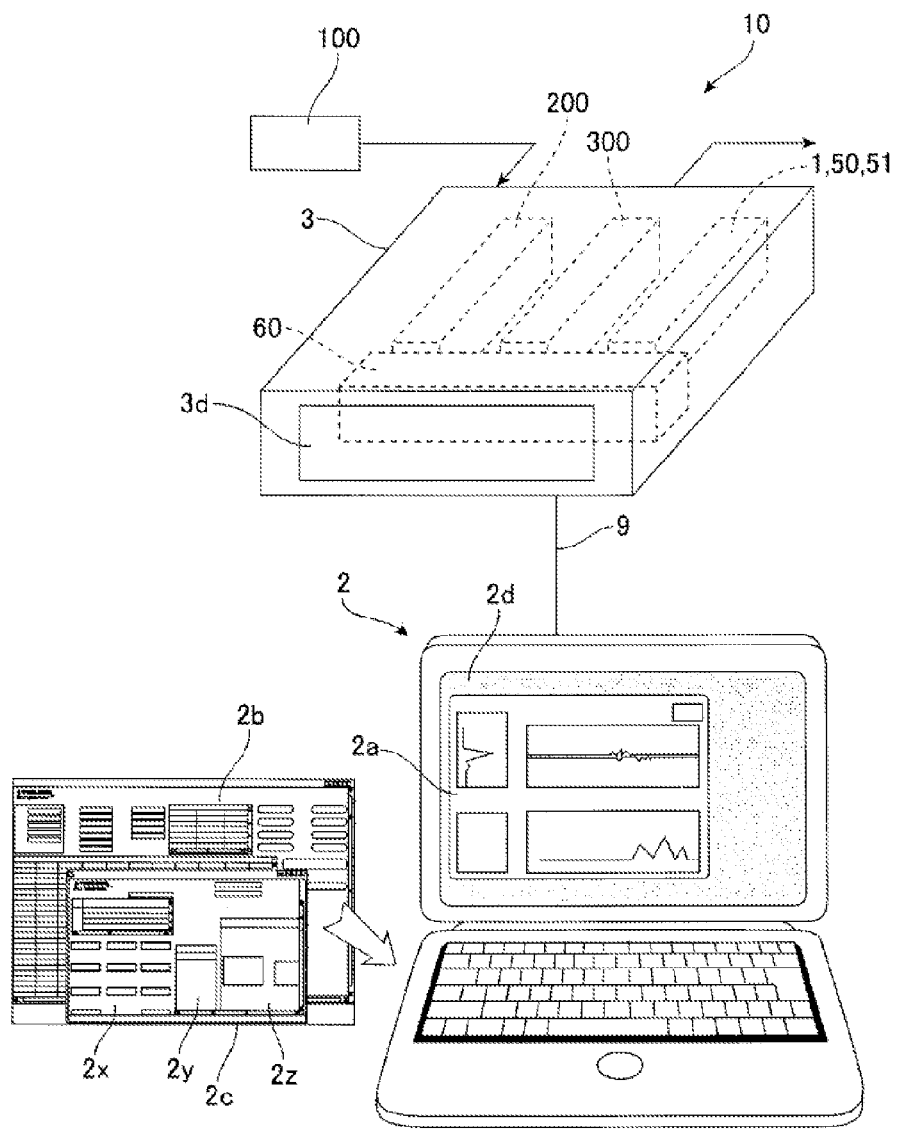
FIG. 5 is a perspective view showing one example of the external appearance of the analysis apparatus.

FIG. 5 shows how the analysis apparatus 10 is housed in a box-like container (housing) 3. The calibration unit 200, the sample preparation unit 300, the ion mobility sensor 1, the discharge-system MFC 50 and the discharge pump 51, and the control unit 60 are housed in this container 3. Such units and parts, including the ion mobility sensor 1, are compact, making it possible to provide the analysis apparatus 10, aside from the sampling unit 100, housed in a container 3 in the form of a cube with sides that are several tens of centimeters or so long. A display 3d for monitoring the operation of the analysis apparatus 10 is provided on the front surface of the container 3.

The analysis apparatus 10 is connected via the network 9 to the terminal 2, which is a personal computer or the like. On the display 2d of the terminal 2, it is possible to display the IMS data 65 as an image 2a, to display a history as an image 2b, and to also display content 2c relating to the IMS data 65. The content 2c can include a plurality of information 2x that is available on the network 9 and corresponds to the plurality of candidates in the IMS data 65, information 2y on the most probable candidates, and information 2z relating to the probable candidate information 2y.

Figure 6:
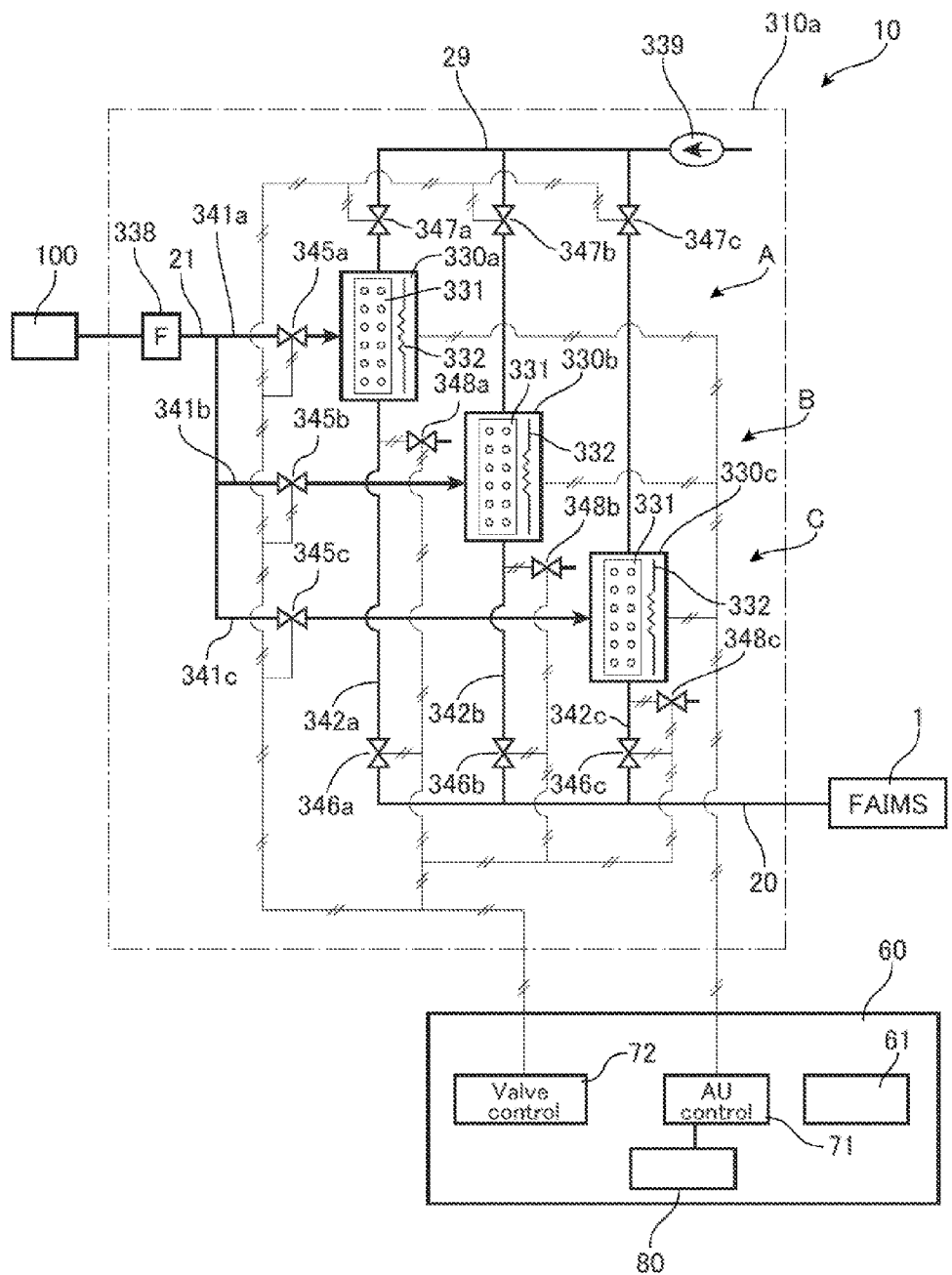
FIG. 6 is a diagram showing another example of a concentration adjusting mechanism.

FIG. 6 shows a different example of the concentration adjusting mechanism 310. The concentration adjusting mechanism 310a includes a plurality of adsorption units (AU) 330a to 330c, a plurality of first paths 341a to 341c that supply the target gas 21 to the respective AU 330a to 330c according to time division, a plurality of second paths 342a to 342c that generate sample gas 20 by releasing adsorbed matter from the respective AU 330 to the carrier gas 29 according to time division, and valves 345a to 345c, 346a to 346c, 347a to 347c, and 348a to 348c that switch the paths. The first path 341, the second path 342, and the valves 345 to 348 should preferably be Teflon (registered trademark) tubes or Teflon-coated components.

The concentration adjusting mechanism 310a switches between the three systems A to C according to time division to concentrate the target chemicals included in the target gas 21 and thereby generate the sample gas 20. Note that although the A system is referred to in the following description as a representative of one system, the operation and the like are the same for the other systems.

The control unit 60 includes an adsorption control unit (AU control unit) 71 that controls the AU 330a to 330c and a valve control unit 72 that controls the valve systems 341 to 348. The AU control unit 71 includes a function that controls the temperature of the adsorption material 331 by controlling a heater 332 included in each of the AU 330a to 330c. The valve control unit 72 includes a function that controls the time for which the adsorption material 331 of the AU 330a to 330c is exposed to the target gas (or "first gas") 21 and a function that controls the plurality of first paths 341a to 341c and the second paths 342a to 342c according to time division.

Figure 7:
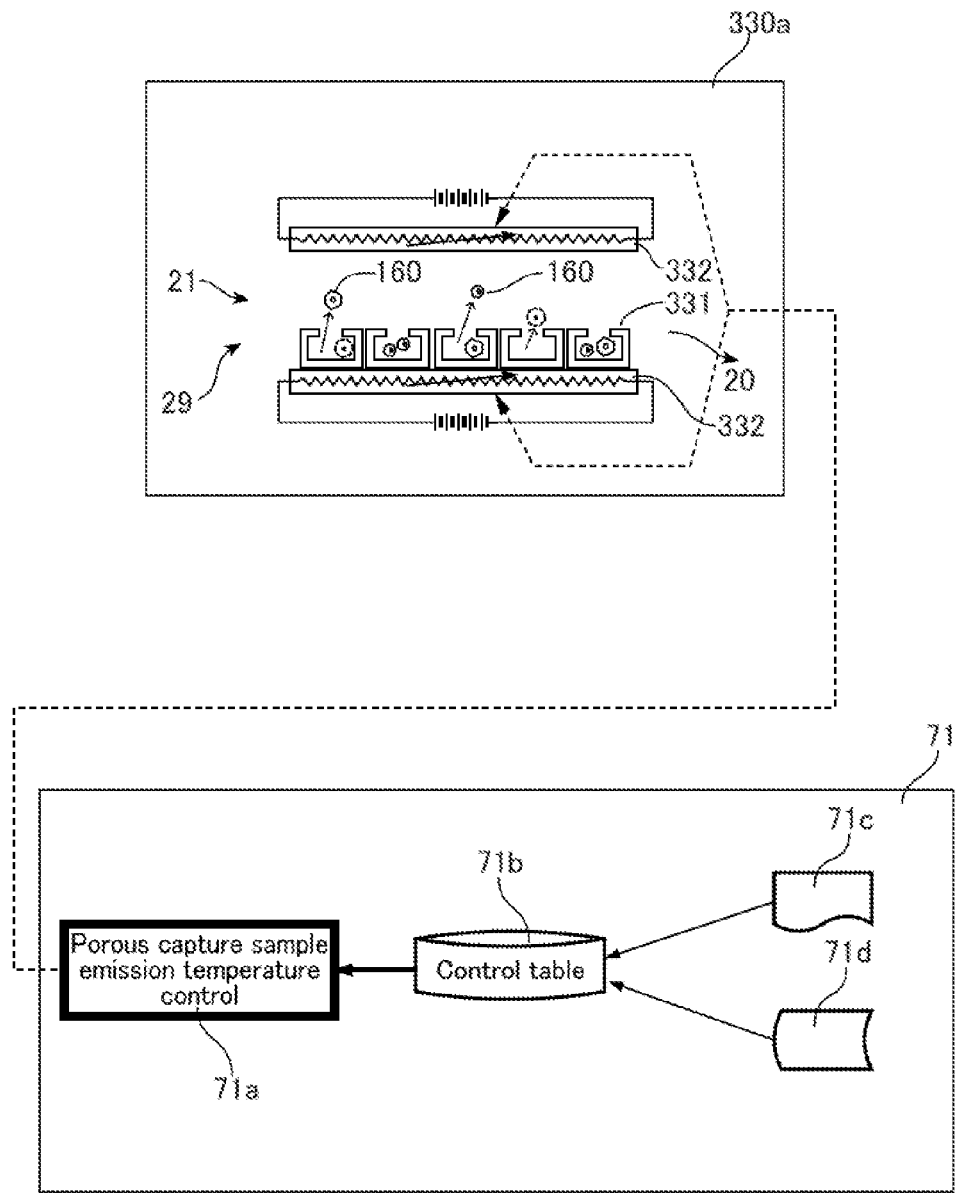
FIG. 7 is a diagram showing one example of an adsorption unit.

FIG. 7 shows one adsorption unit 330a that has been extracted for explanation. For FAIMS technology, it is desirable to improve measurement precision and to do so, it is effectively necessary to efficiently increase the electrical field strength. One solution is to reduce the widths of the plates that apply a voltage to a flight path passed by the sample (sample gas), and by miniaturizing the electrodes of a FAIMS, an effect whereby the FAIMS itself can be made compact is also obtained. On the other hand, since there is an increase in gas flow resistance, it becomes difficult to pass a large amount of sample gas, with it also being important to suppress variations in the flow rate so as to reduce the effects of noise. In addition, it is necessary to prevent infiltration of foreign matter to the sensor 1. That is, filters are disposed to avoid a situation where dust or the like, such as unfavorable particles, is suspended in the sample to be measured and the narrow walls of the Vf/Vc applying electrodes in a FAIMS 1 become covered. However, the filters can cause a pressure drop and variations in the flow rate.

If the sample is clean, such problem will not occur. As one example, by using the adsorption material 331, such as porous glass particles, to capture the sample to be measured (or "target chemical substance" or "target chemical") 160, temporarily stocking the target chemical 160 from the target gas 21 in the adsorption material 331, and emitting the target chemical 160 to clean carrier gas 29, it is possible to measure the target chemical 160 using the sensor 1 without having the target gas 21 flow directly to the sensor 1. In addition, by using the adsorption material 331 to adsorb and discharge the target chemical 160, there is also the merit that it is possible to control the concentration of the target chemical in the sample gas 20.

That is, by applying heat to warm up the adsorption material 331 used as a capture, it is possible to include a low-concentration target chemical (sample) 160 in the sample gas 20 in a concentrated state and also possible to detect the chemical substances to be measured using the sensor 1 even in a case where only a target gas 21 of a low concentration that is far below the measurement limits of the sensor 1 can be obtained. It is possible to obtain the trapping performance and discharge characteristics relative to changes in temperature of the capture (adsorption material) 331 in advance, and by carrying out temperature control of the adsorption material 331 using software, it is possible to have a controlled amount of the target chemical 160 adsorbed by the adsorption material 331 and to have a controlled amount of the target chemical 160 released from the adsorption material 331. Such estimation function is provided in the AU control unit 71, which makes it possible to detect even a target chemical 160 that is sampled at a concentration that makes identification difficult and to ease the limits on the sampling conditions, location, and the like.

A typical example of the adsorption material 331 is porous glass and by selecting the form and size of the pores, it is possible to exclude non-target substances that do not require measurement from the adsorption process.

The AU (sampler) 330 includes the porous adsorption material (capture) 331 that temporally holds (adsorbs) the main constituents (target chemicals) 160 of the target gas 21 before later emitting the target chemicals 160 and a heater for controlling the adsorption and discharge using temperature. The AU control unit 71 includes a controller (porous capture sample discharge temperature control circuit) 71a that controls the heater 332 and a sample emission control table 71b. The table 71b includes information 71c where chemical substances are grouped according to ion mobility and a table 71d showing temperature control according to porous capture size.

The AU control unit 71 controls the temperature of the adsorption material 331 by controlling the output of the heater 332 that heats the adsorption material (capture) 331. A temperature sensor may be installed in the AU 330a and monitored by the AU control unit 71. By having the AU control unit 71 carry out temperature control using the heater 332, it is possible to control emission of the constituents (gas molecules, target chemical) 160 of the target gas 21 primarily held in the adsorption material 331. For example, if the temperature is comparatively low, it is possible to output (release, emit) substances with a low molecular weight or with a small molecular size first from the adsorption material 331 to the carrier gas 29, and by increasing the temperature, substances with a larger molecular weight or with a larger molecular size can then be outputted in order to the carrier gas 29. Accordingly, the temperature of the AU 330 is information that is useful for finding candidate chemical substances from the IMS data 65. For this reason, it is preferable to feed back the temperature of the AU 330 from the AU control unit 71 to the concentration control unit 80 or the terminal 2.

To precisely control the temperature of the adsorption material 331, the heater 332 may include a plurality of heating elements, and as one example it is possible to use a line thermal head.

For a gas that is difficult to sample, such as exhaled air produced by skin respiration or when the concentration of the target chemical substances to be measured is extremely low, the porous capture 331 is effective for pre-concentration and the like. By heating the capture 331 to a high temperature using the heater 332, gas is released as a sample at the measurement stage to the outside and sent to the sensor 1. By selecting the size of the pores in the capture 331, it is also possible to collect the chemical substances to be measured as the target.

Figure 8:
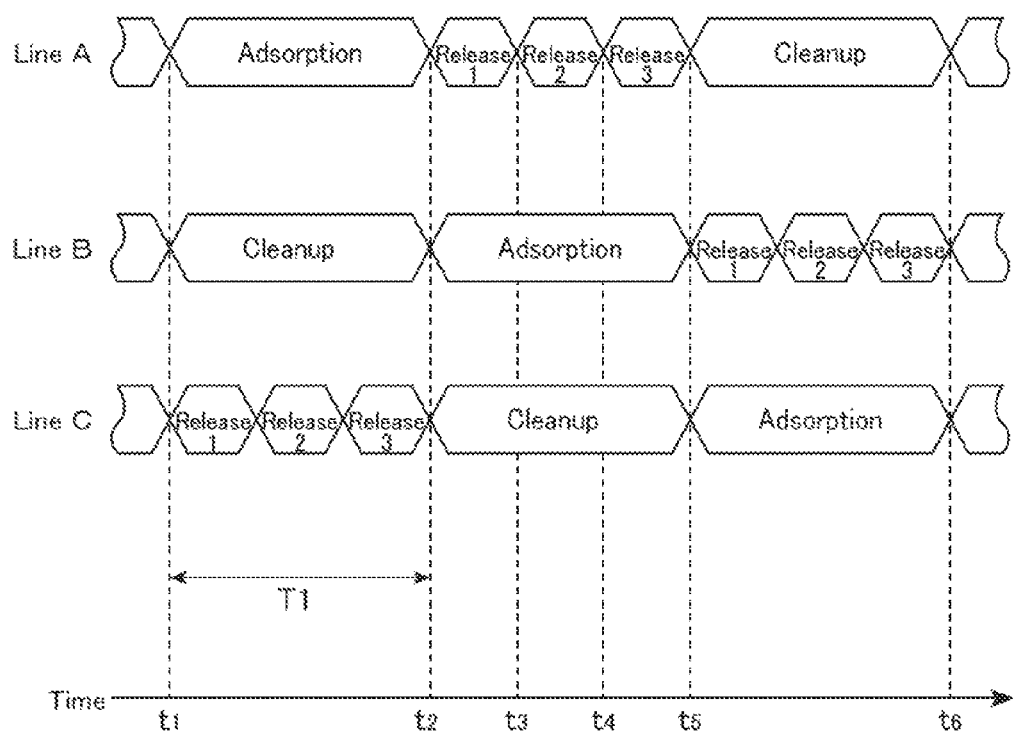
FIG. 8 is a timing chart showing how concentration is controlled using an adsorption unit.

A procedure for continuously capturing the target gas 21 and generating the sample gas 20 by switching between the A, B, and C systems will now be described with reference to FIG. 8. First, at time t1, the valve control unit 72 opens the valve 345a of the first path 341a and the discharge valve 348a of the system A and closes the valve 346a of the second path 342a and the valve 347a for the carrier gas so that the target gas 21 is supplied via the filter 338 to the AU 330a. The AU control unit 71 stops the heater 332 of the AU 330a to set the temperature of the adsorption material 331 at a low adsorption temperature. By doing so, the adsorption material 331 of the AU 330a adsorbs the chemical substances included in the target gas 21.

At a time t2 when a predetermined adsorption period T1 has passed, the valve control unit 72 closes the valve 345a of the first path 341a of the system A and the discharge valve 348a and opens the valve 346a of the second path 342a and the valve 347a of the carrier gas line to supply carrier gas 29 from the carrier gas supply pump 339. The AU control unit 71 heats the adsorption material 331 of the AU 330a using the heater 332 to heat the adsorption material 331 to a first temperature W1. By doing so, out of the chemical substances (target chemicals) 160 adsorbed by the adsorption material 331, constituents that are emitted at a low temperature are released to the carrier gas 29 so that sample gas 20 including a target chemical is supplied to the sensor 1.

At time t3, the AU control unit 71 controls the heater 332 to heat the adsorption material 331 to a second temperature W2 that is higher than the first temperature W1 so that the next constituent is emitted from the adsorption material 331 to the carrier gas 29 and sample gas 20 including the next target chemical is supplied to the sensor 1.

In addition, at time t4, the AU control unit 71 controls the heater 332 to heat the adsorption material 331 to a third temperature W3 that is higher than the second temperature W2 so that the next constituent is released from the adsorption material 331 to the carrier gas 29 and sample gas 20 including the next target chemical is supplied to the sensor 1.

After this, at time t5, the valve control unit 72 closes the valve 345a of the first path 341a of the system A and the valve 346a of the second system and opens the valve 347a of the carrier gas line and the exhaust valve 348a to clean (purge) the AU 330a. The AU control unit 71 heats the adsorption material 331 of the AU 330a using the heater 332 to clean the adsorption material 331. After this, at time t6 the valves and the AU 330a are controlled in the same way as at time t1 to start the adsorption.

Adsorption, emission, and cleaning are repeated in the same way as described above for the line B with a cycle that is shifted by a period T1 with respect to the line A. Adsorption, emission, and cleaning are repeated in the same way as described above for the line C with a cycle that is further shifted by the period T1. Accordingly, the lines A, B and C respectively adsorb the target chemicals from the target gas 21 using the AU 330a to 330c according to time division and also emit target chemicals from the AU 330a to 330c according to time division to generate the sample gas 20.

Accordingly, by using the concentration adjusting mechanism 310a, it is possible to process target gas 21 continuously supplied from the sampling unit 100 and to continuously supply sample gases 20 in which target chemicals have been concentrated to an appropriate concentration to the sensor 1. This means that it is possible to continuously monitor the sampling target even in conditions where only target gas 21 with an extremely low concentration of target chemical can be obtained from the sampling target.

Figure 9:
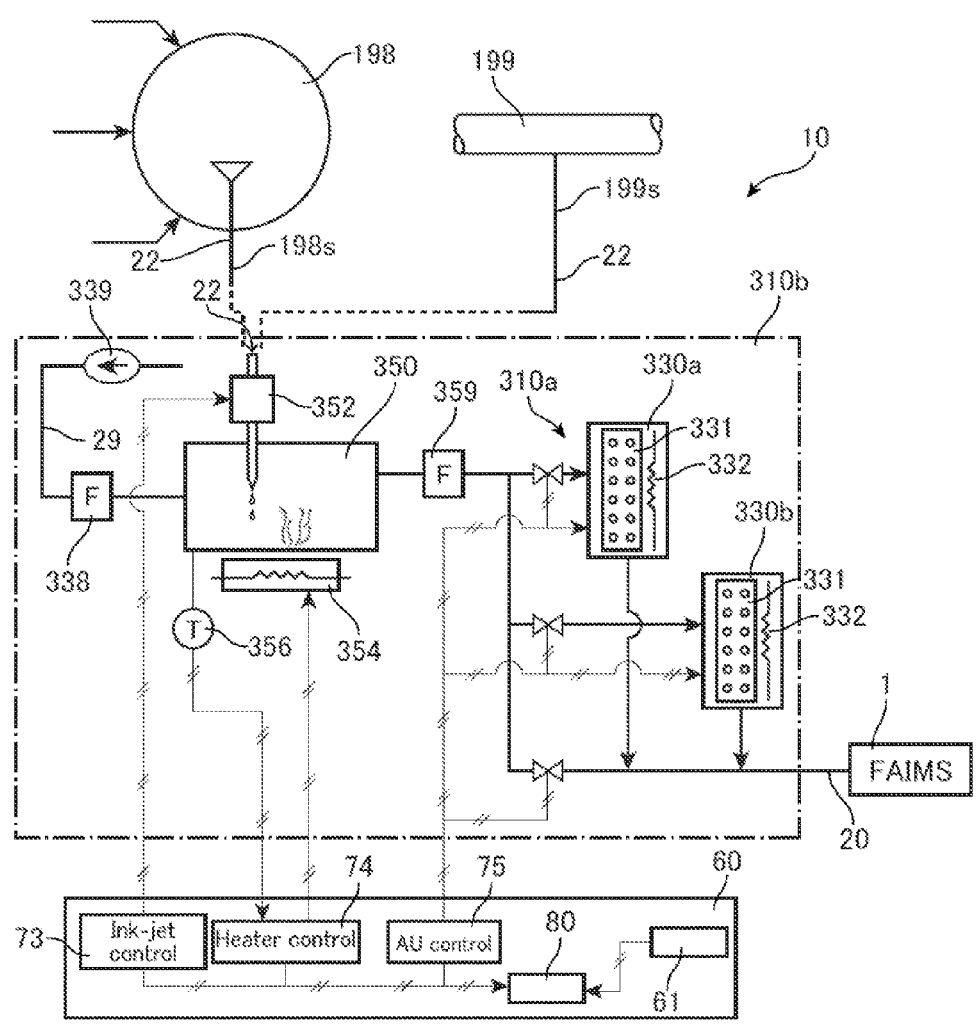
FIG. 9 is a diagram showing another example of a concentration adjusting mechanism.

FIG. 9 shows another example of a concentration control mechanism. Such concentration adjusting mechanism 310b is capable of acquiring a liquid sample (target liquid) 22 from a process pipe 199 or a production tank 198 that manufacture a liquid product and generating sample gas 20 of a suitable concentration for the sensor 1. There may be a plurality of inlet pipes 199s and 198s for acquiring the target liquid 22 from the process pipe 199 and the production tank 198, and the target liquid 22 may be obtained from a plurality of sampling points by switching between the plurality of inlet pipes 199s and 198s using a suitable means.

The concentration adjusting mechanism 310b includes an evaporation chamber 350 that vaporizes a liquid (the target liquid) 22 including the target chemicals to incorporate the target chemicals into the carrier gas 29. The evaporation chamber 350 includes an ink-jet head 352 that discharges the target liquid 22 according to an ink-jet method and a heater 354 that heats the inside of the evaporation chamber 350. The concentration adjusting mechanism 310b also includes an adsorption-type concentration adjusting mechanism 310a that is disposed downstream of the evaporation chamber 350 with a filter 359 in between. The concentration adjusting mechanism 310a is a concentration adjusting mechanism that uses the AU 330a and 330b in the same way as described above.

A liquid amount control mechanism that uses the ink-jet head 352 and an evaporation temperature control mechanism that uses the heater 354 are a number of examples of mechanisms (that is, dilution mechanisms) that control the evaporated amount of the target liquid 22 to incorporate the sampled target liquid 22 into the sample gas 20 (carrier gas 29) with a comparatively low concentration. On the other hand, the adsorption mechanism is a function of concentrating target chemicals. Accordingly, the concentration adjusting mechanism 310b includes a dilution mechanism and a concentration mechanism which means that it is possible to dilute and increase the concentration, in the sample gas 20, of the target chemicals included in an obtained sample.

The control unit 60 includes an ink-jet control unit 73 that controls the amount discharged by the ink-jet head 352, a heater control unit 74 that controls the evaporation temperature of the target liquid 22 by using the heater 354 to heat the inside of the evaporation chamber 350, and a valve/AU control unit 75. The ink-jet head 352 is capable of discharging only a predetermined number of droplets of picoliter or femtoliter units into the evaporation chamber 350 and is capable of controlling the amount of droplets discharged in the evaporation chamber 350 with high precision. Accordingly, even if a target liquid 22 including a high concentration of target chemicals can only be obtained, the concentration adjusting mechanism 310b is capable of generating and supplying to the sensor 1 a sample gas 20 including target chemicals of an order of ppb or ppt that is suited to the sensor 1.

The heater 354 is also use to set the temperature inside the evaporation chamber 350 at a temperature that facilitates evaporation of the target liquid 22. It is also possible to initially set the temperature of the evaporation chamber 350 so that the target liquid 22 is present in the liquid state in the evaporation chamber 350 and to gradually raise the temperature of the evaporation chamber 350 so as to incorporate target chemicals included in the target liquid 22 in order from constituents that are easy to vaporize in the sample gas 20 and supply such sample gas 20 to the sensor 1. Accordingly, the discharged amount of the ink-jet head 352 and the temperature inside the evaporation chamber 350 controlled by the heater 354 are information that is useful in finding candidate chemical substances from the IMS data 65. For this reason, it is desirable for such information to be fed back to the concentration control unit 80 or the terminal 2. In addition, it is also effective to install a sensor 356 and monitor the temperature, pressure, flow rate, and the like inside the evaporation chamber 350.

The analysis system 10 including the concentration adjusting mechanism 310b is capable of adjusting concentration while sampling in real time in the same way as the system 10 that includes the concentration adjusting mechanism 310a described earlier. In addition, the analysis system 10 that includes the concentration adjusting mechanism 310b is capable of analyzing liquids as a target and is compatible with water quality tests and applications that have liquids, such as pharmaceuticals and foodstuffs, as products. In addition, for an application that has solids as products, the analysis system 10 is capable of being applied by liquefying the solids by dissolving the solids in a suitable liquid (solvent), by vaporizing the solids according to an appropriate method, or by detecting volatile components outputted from the products.

Figure 10:
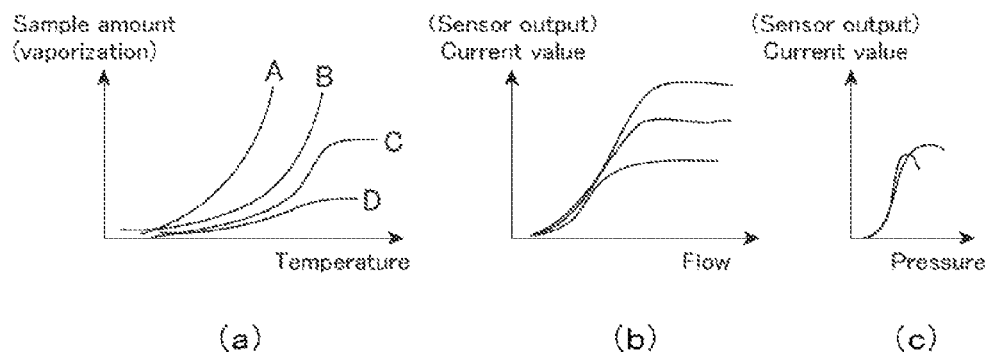
FIG. 10($a$) is a diagram showing how a vaporization amount changes according to temperature, FIG. 10($b$) is a diagram showing how a measurement value changes according to flow rate, and FIG. 10($c$) is a diagram showing how a measurement value changes according to pressure.

FIG. 10 schematically shows how the state changes according to a sample. As shown in FIG. 10(a), the temperature dependence of the vaporized amount will change according to the sample. As shown in FIG. 10(b), the output (current value) of the sensor 1 will change according to the flow rate of the sample gas 20. In addition, as shown in FIG. 10(c), the output of the sensor 1 will change according to the air pressure where the sensor 1 is set up. Accordingly, there are many cases where it is not easy to acquire reproducible data using the sensor 1. On the other hand, information on the variation tendencies, variation range, and the like of the output of the sensor 1 is characteristics of the target chemicals with respect to the sensor 1. Accordingly, automatic adjustment carried out by the concentration adjusting mechanism 310 to a concentration where the target chemicals can be detected by the sensor 1 and the result of such adjustment (control information) is important information for specifying the target chemicals.

Figure 11:
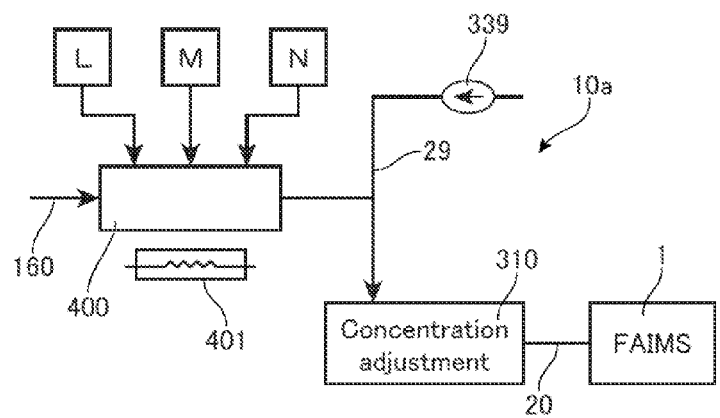
FIG. 11 is a diagram showing another example of an analysis apparatus.

FIG. 11 shows a different example of an analysis apparatus. This analysis apparatus 10a includes a reaction chamber 400 and a heater 401 that controls the temperature of the reaction chamber 400. The reaction chamber (chemical reaction chamber) 400 causes a reaction between a composition (target chemicals) 160 to be analyzed and other compositions L, M, and N to convert to a composition including a target chemical (a first constituent) that can be analyzed by the sensor 1. The secondary chemical produced by the conversion is supplied by a carrier gas 29 supplied from a carrier gas supply pump 339 to the concentration adjusting mechanism 310 and after adjustment of the concentration, the secondary chemical is supplied as the sample gas 20 to the sensor 1.

The analysis apparatus 10a equipped with the reaction chamber 400 is capable of analysis that has a chemical substance which is difficult for the sensor 1 to directly measure as a target. It is desirable for the chemical substance (secondary chemical) used for indirect measurement to be a substance that is not included in the background or which is present in the background in very small amounts. Accordingly, it is desirable to carry out measurement of the baseline and background of the sensor 1 before indirect measurement and then decide the concentration and amount of the chemical substance to be indirectly measured. Even if the secondary chemical used in the indirect measurement is present in the background, by comparing (i.e., finding the difference between) measurement results including the directly measured secondary chemical and measurement results including the secondary chemical obtained from the reaction chamber 400, it is possible to specify and analyze the chemical substance that is actually to be measured. As one example, when measuring ammonia (NH3) alone, there are cases where the measurement results will be affected by other chemical substances included in the background. If it is difficult to measure ammonia alone, it is possible to mix with a ketoglutarate acid and dehydrogenase (GDH) to produce glutamic acid and to measure such produced chemical substance (secondary chemical) to identify and perform quantitative analysis on the ammonia.

Indirect measurement is effective for chemicals that carry the risk of corroding or breaking the sensor 1 such as highly corrosive chemical substances as concentrated sulfuric acid, for explosive chemical substances, and for harmful chemical substances for which exhausting is problematic. By carrying out measurement while changing such substances into chemical substances that can be safely measured, it is possible to measure a variety of chemical substances safely and reliably with the sensor 1 and to identify the presence of, and perform quantitative analysis on, such substances.

Figure 12:
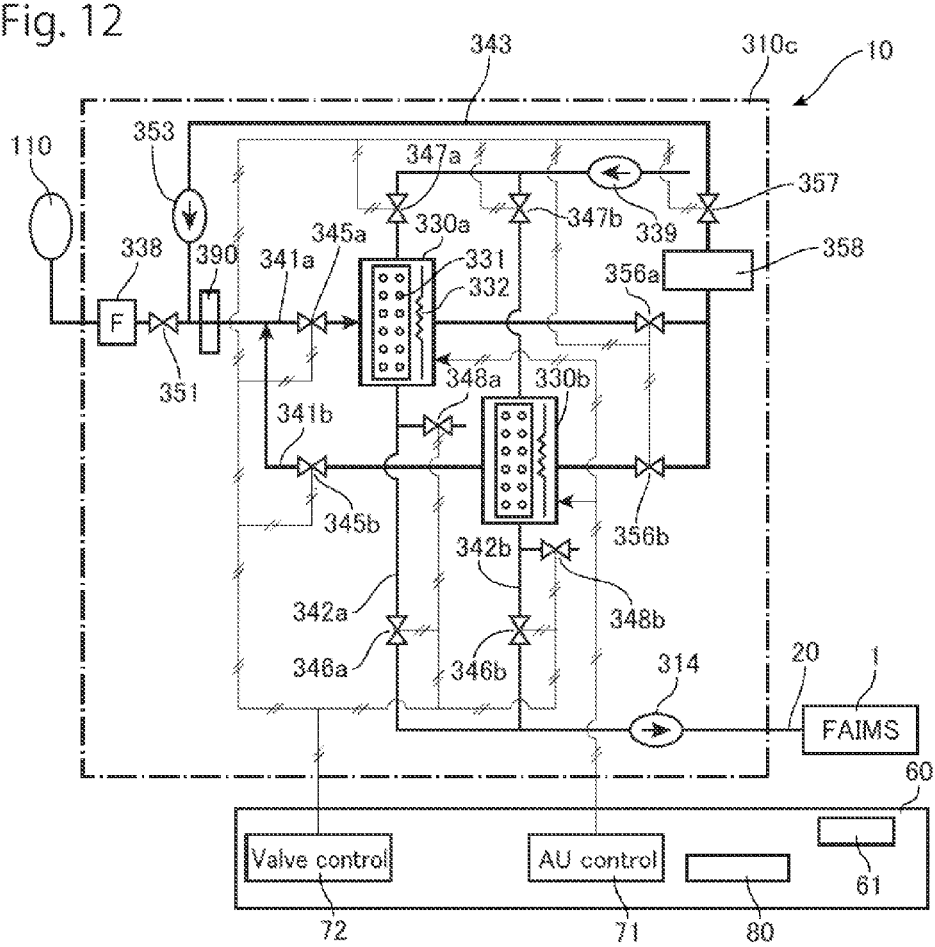
FIG. 12 is a diagram showing another example of a concentration adjusting mechanism.

FIG. 12 shows another example of a concentration adjusting mechanism. This concentration adjusting mechanism 310c includes, in addition to the first paths 341a and 341b and the second paths 342a and 342b described for the concentration adjusting mechanism 310a given above, a third path 343 that feeds the first gas (target gas) 21 back to the first path 341a and 341b. By supplying low concentration target gas 21 a plurality of times via the feedback route 343 to the AU 330a and 330b, it is possible to accumulate the target chemicals included in the target gas 21 in the adsorption material 331, such as porous glass. During measurement, the number of feedback iterations is stored in advance, the second paths 342a and 342b are opened, the temperatures of the AU 330a and 330b are raised, and the target chemical accumulated in the adsorption material 331 is emitted all at once to the carrier gas 29 to produce sample gas 20 with a high concentration.

In this example, the AU 330a and 330b are connected in parallel and when the target gas 21 is supplied from a tank 110 to the concentration adjusting mechanism 310c, the inlet valve 351 is closed, the valves 356a, 356b, and 357 of the third path (the feedback loop) 343 are opened, the recycling pump 353 is driven, and the target gas 21 is recycled via the feedback loop 343. A buffer 358 is provided on the feedback loop 343 so that it is possible to maintain the flow rate for recycling.

After the target gas 21 has been recycled for the predetermined period, in the same way as with the concentration adjusting mechanism 310a described earlier, the carrier gas 29 is supplied to the AU 330a and 330b to generate the sample gas 20.

This concentration adjusting mechanism 310c further includes a removal unit 390 that removes compositions (second compositions) aside from the target chemicals from the target gas 21 that is being recycled. The removal unit 390 is a cold trap, for example, and is capable of removing moisture. Another example of the removal unit 390 is porous glass where the pore diameter is controlled. By selecting porous glass that is suited to adsorbing chemicals aside from target chemicals to be adsorbed by the AU 330a and 330b and using such porous glass in the removal unit 390, it is possible to effectively accumulate the target chemical in the AU 330a and 330b. The removal unit 390 may be a unit that removes oxygen, carbon dioxide, and/or nitrogen present in air.

The analysis apparatus (analysis system) 10 described above is capable of automatically adjusting the concentration of the sample gas 20. Accordingly, it is possible to carry out measurement and analysis even for a target with a low concentration or a high concentration for which it is difficult to obtain reliable measurement results through direct measurement with the ion mobility sensor 1 without excluding such targets from analysis or detection. This means that it is possible to use FAIMS technology in even more applications and to apply FAIMS technology to the monitoring of liquid processes and the monitoring of water treatment.

The invention claimed is:

1. An apparatus comprising:
a unit of preparing a sample to be supplied to an ion mobility sensor; and
a control unit including a function for controlling the unit of preparing,
wherein the unit of preparing includes a concentration adjusting mechanism changing a concentration of a first constituent included in the sample, and
the control unit includes a function of acquiring a measurement result of the ion mobility sensor and a function of controlling the concentration adjusting mechanism in a direction in which the measurement result improves, and
the function for controlling the concentration adjusting mechanism includes:
a function of preliminarily analyzing measurement results obtained by controlling the concentration adjusting mechanism so as to change the concentration of the first constituent in stages and selecting a chemical substance candidate included in the first constituent; and
a function of accessing a database of a plurality of chemical substances that are to be measured by the ion mobility sensor and includes data on concentrations of each of the plurality of chemical substances that are suited to detection by the ion mobility sensor to acquire a detection concentration suited to detecting the chemical substance candidate and controlling the concentration adjusting mechanism so that a concentration of the first constituent included in the sample becomes the detection concentration.

2. The apparatus according to claim 1,
wherein the control unit includes a function of outputting control information outputted to the concentration adjusting mechanism.

3. The apparatus according to claim 1,
wherein the concentration adjusting mechanism includes an adsorption material that adsorbs the first constituent and a mechanism that heats the adsorption material to release the first constituent adsorbed by the adsorption material to a carrier gas, and
the control unit includes a function of controlling the temperature of the adsorption material.

4. The apparatus according to claim 3,
wherein the concentration adjusting mechanism further includes a first path where a first gas that includes the first constituent passes the adsorption material and a second path where a constituent adsorbed by the adsorption material is released to the carrier gas, and
the control unit includes a function of controlling a period for which the adsorption material is exposed to the first gas.

5. The apparatus according to claim 4,
wherein the concentration adjusting mechanism includes a plurality of the first paths and the second paths, and
the control unit includes a function of controlling the plurality of the first paths and the second paths according to time division.

6. The apparatus according to claim 3,
wherein the concentration adjusting mechanism includes a third path feeding back the first gas to the first path.

7. The apparatus according to claim 3,
wherein the adsorption material is porous glass.

8. The apparatus according to claim 1,
wherein the concentration adjusting mechanism includes a mechanism that generates the sample including the first constituent by heating a liquid including the first constituent, and
the control unit includes a function of controlling a heating temperature of the liquid including the first constituent.

9. The apparatus according to claim 1,
wherein the concentration adjusting mechanism includes a mechanism that generates a sample including the first constituent by ejecting a liquid including the first constituent according to an ink-jet method, and
the control unit includes a function of controlling the ejected amount of liquid including the first constituent.

10. The apparatus according to claim 1,
wherein the concentration adjusting mechanism includes a mechanism that removes a second constituent from the first gas including the first constituent.

11. The apparatus according to claim 1,
wherein the sample includes air or a carrier gas with known constituents,
the concentration adjusting mechanism includes a flow amount control mechanism of injecting a first gas including the first constituent into the carrier gas, and
the control unit includes a function of changing a mixing ratio of the first gas and the carrier gas using the flow amount control mechanism.

12. The apparatus according to claim 1,
further comprising a mechanism causing a chemical substance to be analyzed to react with another chemical substance to convert to the first constituent.

13. The apparatus according to claim 1,
further comprising a gas collecting apparatus that collects gas to be analyzed which includes the first constituent and supplies the gas to the concentration adjusting mechanism,
wherein the gas collecting apparatus includes:
a unit that controls an air amount forming an air curtain; and
a unit that collects the gas to be analyzed from a region surrounded by the air curtain,
and the control unit includes a function of controlling, in cooperation with the concentration adjusting mechanism, the air amount forming the air curtain.

14. The apparatus according to claim 1,
further comprising the ion mobility sensor; and
a processing unit that obtains an analysis result based on an output of the ion mobility sensor and control information sent to the concentration adjusting mechanism.

15. The apparatus according to claim 14,
further comprising a calibration unit that incorporates a pilot constituent including a known chemical substance into the sample.

16. The apparatus according to claim 15,
wherein the calibration unit supplies the sample including the pilot constituent as the first constituent to the concentration adjusting mechanism.

17. A control method for an apparatus including a unit of preparing a sample to be supplied to an ion mobility sensor and a control unit controlling the unit of preparing, the unit of preparing including a concentration adjusting mechanism changing a concentration of a first constituent included in the sample,
the control method comprising:
the control unit receiving a measurement result from the ion mobility sensor; and
the control unit controlling the concentration adjusting mechanism in a direction in which the measurement result improves, and
controlling the concentration adjusting mechanism includes:
preliminarily analyzing measurement results obtained by controlling the concentration adjusting mechanism so as to change the concentration of the first constituent in stages and selecting a chemical substance candidate included in the first constituent; and
accessing a database of a plurality of chemical substances that are to be measured by the ion mobility sensor and includes data on concentrations of each of the plurality of chemical substances that are suited to detection by the ion mobility sensor to acquire a detection concentration suited to detecting the chemical substance candidate and controlling the concentration adjusting mechanism so that a concentration of the first constituent included in the sample becomes the detection concentration.

18. An apparatus comprising:
a unit of preparing a sample to be supplied to an ion mobility sensor; and
a control unit including a function of controlling the unit for preparing,
wherein the unit of preparing includes a concentration adjusting mechanism changing a concentration of a first constituent included in the sample, and the control unit includes a function of acquiring a measurement result of the ion mobility sensor and a function of controlling the concentration adjusting mechanism in a direction in which the measurement result improves, the apparatus further comprises a gas collecting apparatus that collects gas to be analyzed which includes the first constituent and supplies the gas to the concentration adjusting mechanism, the gas collecting apparatus includes:

a unit that controls an air amount forming an air curtain; and a unit that collects the gas to be analyzed from a region surrounded by the air curtain, and the control unit includes a function of controlling, in cooperation with the concentration adjusting mechanism, the air amount forming the air curtain.

* * * * *